United States Patent [19]

Saito et al.

[11] 4,337,038
[45] Jun. 29, 1982

[54] ELECTROLYTIC IMPLEMENT AND METHOD FOR REMOVING METAL PIECES LEFT IN ROOT CANALS OF TEETH

[75] Inventors: Tsuyoshi Saito; Masaru Ogiwara, both of Tokyo, Japan

[73] Assignee: M-S Surgical Mfg. Co., Ltd., Tokyo, Japan

[21] Appl. No.: 199,368

[22] Filed: Oct. 21, 1980

[30] Foreign Application Priority Data

Nov. 19, 1979 [JP] Japan .................................. 54-148881

[51] Int. Cl.³ .............................................. A61C 3/00
[52] U.S. Cl. ................................... 433/32; 128/303.1; 204/224 R; 204/129.6
[58] Field of Search ................. 433/32, 141, 102, 136; 128/737, 303.1, 303.13; 204/288, 289, 224 R, 129.6, DIG. 6

[56] References Cited

U.S. PATENT DOCUMENTS

| 525,797 | 9/1894 | Richmond | 433/136 |
|---|---|---|---|
| 1,509,161 | 9/1924 | Maurer | 433/32 |
| 2,121,875 | 6/1938 | Kruse et al. | 433/32 |
| 2,276,623 | 3/1942 | Meiman | 433/32 |
| 2,516,882 | 8/1950 | Kalom | 128/737 |
| 2,784,155 | 3/1957 | Heinrich | 204/224 R |
| 3,078,850 | 2/1963 | Schein et al. | 128/303.13 |
| 3,322,124 | 5/1967 | Ireland | 433/141 |

FOREIGN PATENT DOCUMENTS

2806297 8/1979 Fed. Rep. of Germany ........ 433/32
53-26079 7/1978 Japan ................................... 433/102

OTHER PUBLICATIONS

Masserann Brochure, p. 7, line 13 to 26, and p. 7, line 35 to p. 8, line 10, 1971.

*Primary Examiner*—Paul J. Hirsch
*Assistant Examiner*—John J. Wilson
*Attorney, Agent, or Firm*—Lowe, King, Price & Becker

[57] ABSTRACT

In an electrolytic method of and implement for removing metal pieces left in root canals of teeth, a metal needle as the positive electrode and a metal pipe as the negative electrode are used to establish an electrolytic reaction within the root canals to dissolve the metal pieces. The metal pipe is fitted about the metal needle in such a way as to be adapted to slide back and forth on the needle. The metal needle and the metal pipe end has an outer surface, thereof except its tip portion, coated with an electrically insulating material, and a hole for supplying an electrolyte is formed within the metal needle. An electrolytic cell is created in the root canal containing a metal piece by inserting the needle into the canal until it contacts the metal piece with the metal tube spaced above. Electrolyte is supplied to the root canal between the two electrodes (needle and tube) and a voltage is applied therebetween to dissolve the metal piece by electrolysis.

10 Claims, 4 Drawing Figures

F I G. 2
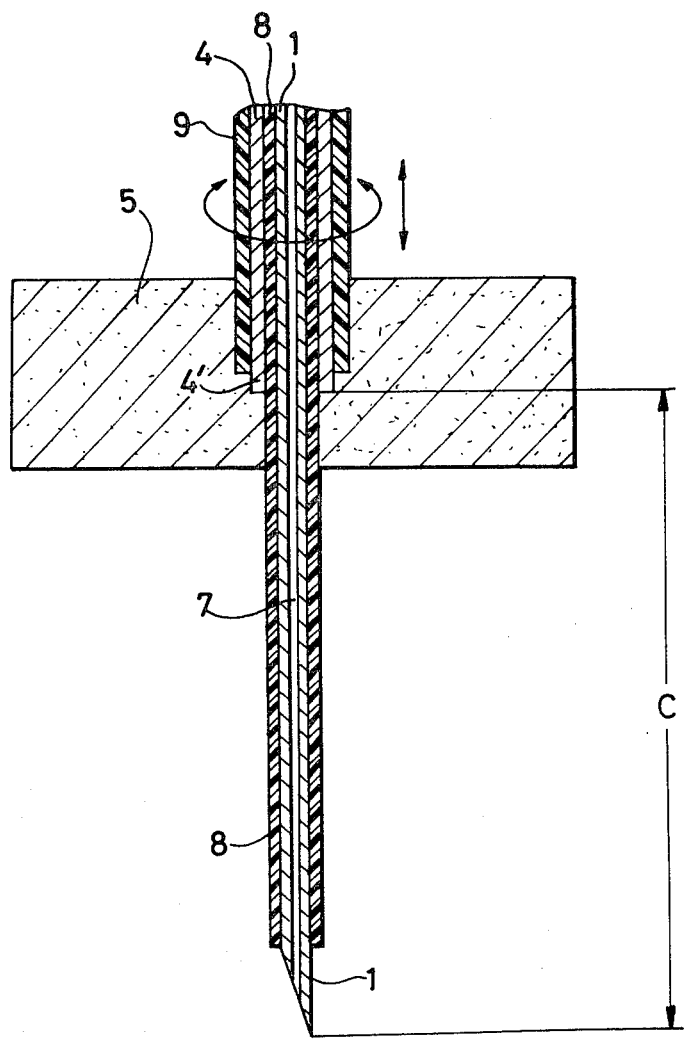

ELECTROLYTIC IMPLEMENT AND METHOD FOR REMOVING METAL PIECES LEFT IN ROOT CANALS OF TEETH

BACKGROUND OF THE INVENTION

1. Field of the Invention

The present invention relates to a method of and an electrolytic implement for removing metal pieces such as dental reamers, files or broaches, left in root canals of teeth.

2. Description of the Prior Art

It often happens when carrying out root canal treatment of teeth that a dental appliance such as a reamer, a file, or a broach is broken in a root canal leaving a metal piece. For removal of such residual metal pieces from root canals, there have heretofore been adopted various unpleasant mechanical, chemical and surgical methods.

As an example of a mechanical method presently in use called a Massellan method, the dentine around the residual metal piece is cut off using a special hollow cutting instrument. A special gripping implement is then inserted into the void formed between the residual metal piece and the dentine. Then the top end of the separated metal piece is gripped by the gripping instrument and the metal piece is withdrawn. In this method, the presence and removal should be confirmed by means of radiograph. A long time is required for removal by this method, after a couple of hours. Moreover, application of this method is difficult when the residual metal piece is sharply pointed or the root canal is flat, and if the root canal is curved, this method cannot be applied.

As an example of a chemical method, an iodine method previously practiced uses a potassium iodide or iodine trichloride solution. According to this method, it is necessary to form a by-pass around the residual metal piece to facilitate dissolving the separated metal piece by the solution. Furthermore, if the separated metal piece is relatively large, a long time is required for corrosion of the metal piece and dissolution is often not completed within the time allocated for one treatment. Therefore, in such a case, the chemical solution is sealed in the root canal and after a period of 3 to 7 days, the corroded residual metal piece is removed by a reamer or file. If corrosion is insufficient and such removal by the reamer or file is impossible, the chemical solution is applied again and the above treatment is repeated.

In each of the above-mentioned two methods, a high level of skill is required by the dentist and the patient experiences a lot of discomfort. Moreover, at least several hours are necessary for completion of the removal treatment and in some cases, the treatment extends over 2 or 3 weeks. Furthermore, even after employing these methods, removal is sometimes impossible.

SUMMARY OF THE INVENTION

It is, therefore, a primary objective of the present invention to provide a method of and instrument for removing broken metal pieces left in root canals of teeth in a relatively short period of time without high level of skill, irrespective of the position or the state of the residual metal piece; all while the patient experiences little or no discomfort.

The instrument of the present invention comprises a metal needle acting as a positive electrode inserted into the root canal of a tooth and brought into contact with the separated metal piece. A metal tube acting as a negative electrode is arranged around the needle with the needle capable of sliding and rotating within the tube. Except for the top portion thereof, the tube is coated with an electrically insulating material.

In accordance with the method of the invention, the tip of the metal needle (the positive electrode) is inserted into the root canal and is brought into contact with the metal piece left in the root canal. At the same time the metal tube (the negative electrode) is fitted into the inlet portion of the root canal through an absorbent material such as cotton. An electrolyte is placed in the root canal and an appropriate direct current voltage is applied between both electrodes to effect electrolysis. The metal piece left in the root canal is thereby dissolved in the electrolyte.

BRIEF DESCRIPTION OF THE DRAWINGS

FIG. 2 is an enlarged sectional view showing a part of the electrolytic implement shown in FIG. 1;

DETAILED DESCRIPTION OF THE PREFERRED EMBODIMENTS

Figure 1:
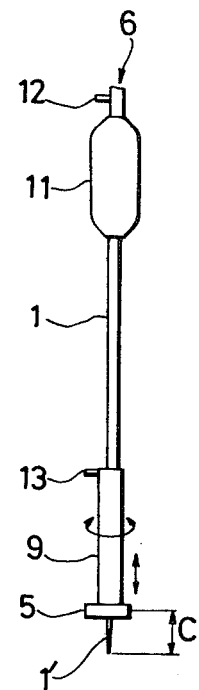
FIG. 1 is a front view of an embodiment the electrolytic implement according to the present invention.

Referring to FIGS. 1 and 2, the electrolytic implement of the present invention comprises a metal needle 1 as a positive electrode and a metal pipe 4 as a negative electrode. The metal needle 1 has a predetermined portion of the outer surface, except the tip portion 1' thereof, covered with an electrically insulating coating 8 composed of polyvinyl chloride. A continuous hole 7 (FIG. 2) for supplying an electrolyte is formed along the central axis of the metal needle 1. The metal pipe 4 is fitted around the metal needle 1 over the polyvinyl chloride coating 8 so that the metal tube can freely slide, rotate and stop. The metal pipe 4 has a predetermined portion of its outer surface, except the tip end portion 4' thereof, covered with an electrically insulating coating 9 composed of polyvinyl chloride. The shaft portion of the metal needle 1 (positive electrode) extends outwardly from the metal tube 4 (negative electrode) and a grip 11 is formed on the top end of the shaft portion of the metal needle 1. A conductive line-connecting terminal 12 is formed on the upper portion of the metal needle 1 as the positive electrode and another conductive line-connecting terminal 13 is formed on the top end of the metal pipe 4 as the negative electrode. A piece of absorbent material 5 is attached to the tip end portion of the metal pipe 4 (negative electrode) so that when the implement is used, the absorbent piece is fitted snugly into the inlet portion of the root canal of a tooth to close the inlet portion. The absorbent piece 5 can be ordinary cotton or porous elastomer composed of a synthetic resin.

An aqueous solution of sodium chloride is used as the aforementioned electrolyte. Accordingly, both the positive and negative electrodes of the electrolytic instrument are made of a platinum-rhodium alloy. Since an aqueous solution of sodium chloride is used as the electrolyte, a chloric acid salt precipitate is formed around the tip portion 1' of the positive electrode 1 and in the vicinity of the residual metal piece during the electrolysis, whereby dissolution of the residual metal piece is promoted. Accordingly, the electrolyte around the tip portion of the tube 4', is rendered alkaline. The platinum-rhodium alloy has high resistance and durability against these electrochemical reactions. For this reason, the platinum-rhodium alloy is used as the electrode material.

In cases of curved roots the needle portion 1 (positive electrode) must often engage narrow and difficult canals to make contact with the broken metal piece. In order to satisfy this requirement, the metal needle 1 should have appropriate firmness and flexibility. Moreover, the metal needle 1 (positive electrode) has a shape of a fine pipe and the ability to shape and process such a configuration from the material is very important.

By experimentation, it was confirmed that if the alloy of the electrode consists of 60-90% platinum and 10-40% rhodium by weight, all of the foregoing requirements are satisfied and optimum results can be obtained. All the parts of the metal needle 1 and the metal pipe 4, except for the tip portion, may be coated with an electrically insulating material.

The absorbent piece 5 should have a softness sufficient to cover the inlet portion of the root canal of a tooth having an indefinite shape and size and also should have a capacity to absorb sufficient electrolyte to facilitate movement of ions during the electrolysis. When substances dissolve out of the residual metal piece during electrolysis and are discharged into and out of the root canal, they are converted to various precipitates in the vicinity of the negative electrode. Accordingly, the absorbent piece 5 should have a filtering capacity sufficient to collect these precipitates. A rolled and shaped piece of absorbent cotton satisfies all of the foregoing requirements, can easily be changed and is excellent in softness and water-absorption over other similar materials such as synthetic fibers and foamed plastics. Furthermore, the safety of absorbent cotton as a medical material has been confirmed. In view of the foregoing, absorbent cotton is preferred for the use as the absorbent piece 5 that is used in the present invention.

Polyvinyl chloride is preferred as the coating material 8 and 9 of both electrodes. Among plastic materials, polyvinyl chloride is most suitable for forming a coating around the fine pipe. Polyvinyl chloride has the appropriate elasticity and the suitable slip friction to a metal. Accordingly, relative sliding movement between the inner face of the negative electrode tube 4 and the positive electrode coating 8 is facilitated and the electrode assembly can be firmly set to the root canal of the tooth. Moreover, coatings of polyvinyl chloride are excellent in strength, flexibility, electrical insulating property and chemical resistance. Therefore, among various plastic materials, polyvinyl chloride is preferred for use as electrode coating in the present invention.

Figure 3:
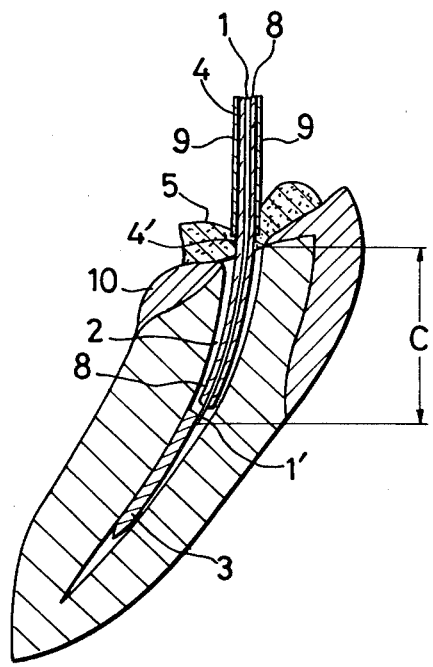
FIG. 3 is an illustration in cross section showing correct positioning of the electrolytic instrument relative to a broken metal piece within the root canal.

FIG. 3 is a diagram illustrating the relative location of the implement when in actual use within the root canal. During the electrolysis process, it is preferred that the tip portion 4' of the metal pipe 4 (negative electrode) be located as close as possible to the residual metal piece 3. For this reason, the distance C between the tips of the two electrodes is initially set at 3 mm, although this distance can be increased as necessary by sliding the tube up along the needle. The absorbent piece 5 is attached to the tip portion 4' of the metal pipe 4 (negative electrode). Then the tip portion 1' of the metal needle 1 (positive electrode) is inserted into the root canal. This insertion operation is carried out by manually grasping the grip 11 in the upper portion of the electrolytic implement shown in FIG. 1. The positive and negative electrodes are fitted to each other so that they can be slid and rotated relative to each other and an appropriate amount of friction is produced therebetween. Then the tip portion 4' with the absorbent piece 5 already attached is placed at the inlet portion of the root canal. By applying compressive and rotational forces, the needle 1 (positive electrode) is now slid through the stationary tube 4 and the tip of the needle 1' is brought into contact with the residual metal piece 3. Then the electrolyte is introduced into the root canal through the hole 7 coursing through the positive electrode 1 and an appropriate voltage is applied between the electrodes by a power source circuit shown in the schematic diagram of FIG. 4 to effect electrolysis.

As is apparent from the structure of the electrolytic implement heretofore described that the portion of each electrode coming into contact with the electrolyte is very small, and that the electrolysis process occurs only within the confines of the root canal 2. The direct current electrolysis voltage is 3 to 5 V and the electrolysis current is 2 to 20 mA. This level is, by any means, nowhere near enough to cause any discomfort to the patient. Needless to say, safety to the human body has been amply considered with respect to the power source device. Moreover, the electrolyte, that is, an aqueous solution of sodium chloride, has good electric conductivity and is safe to the human body.

Since the electrolyte is supplied into the root canal 2 via the hole 7 coursing through the positive electrode 1, the electrolyte can easily be introduced even into a narrow portion of the root canal 2. Furthermore, the electrolyte can be supplied in the state where the electrolytes are set. As electrolysis continues within the root canal, various substances and gases are generated from the electrodes and the residual metal piece and tend to decrease the effectiveness of the electrolysis process. However, this is remedied by the presence of the absorbent piece 5 through which these inhibitive materials are discharged and ideal electrolysis conditions are maintained. Hence the operation of dissolving and removal of broken metal pieces is simplified and shortened.

The ions and compounds formed in the electrolyte are deposited on the absorbent piece 5 while the spent electrolyte is discharged from the root canal 2 with a supply of fresh electrolyte.

Figure 4:
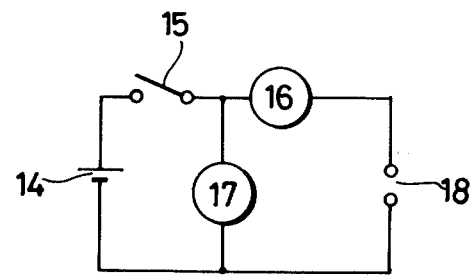
FIG. 4 is a schematic diagram illustrating a power source circuit for the electrolytic implement of FIGS. 1 and 2.

FIG. 4 is a circuit diagram of the power source device for the electrolytic implement of the present invention. In FIG. 4, reference numerals 14, 15, 16, 17 and 18 represent, respectively, a battery, a switch, an electrolysis current indicator, an electrolysis voltage indicator and a terminal for supplying an electric current to the electrodes of the electrolytic implement of the present invention.

In the foregoing description, the hole 7 for supplying the electrolyte is formed within the metal needle (positive electrode). In the present invention, an electrolyte supply pipe may be formed independently instead of such hole 7.

Excellent effects attained by the electrolytic implement of the present invention will be apparent from the results of the following experiments of removing residual metal pieces by electrolysis.

EXPERIMENTAL CONDITIONS

Sample teeth:
4 extracted human front teeth (since the sample teeth were dry, they were dipped in a physiological saline solution for 12 hours before the experiment, and metal pieces were set in the root canals at points about 8 mm from the inlet portions of the root canals)
Residual metal pieces:
reamers of SUS 304 having a length of 10 mm and a weight of 10 to 12 mg
Electrolyte:
10% by weight aqueous solution of sodium chloride
Electrode metal:
alloy comprising 60% by weight of platinum and 40% by weight of rhodium
Electrolysis voltage:
4.5 V (direct current)
Power source:
dry cell The electrolysis was carried out under the abovementioned conditions to obtain results shown in Table 1.

TABLE 1

|  | Electrolysis Time (minutes) | | | |
| --- | --- | --- | --- | --- |
|  | 10 | 20 | 30 | 40 |
| Dissolution ratio (%) | 40 | 70 | 90 | 100 |
| Electrolysis current (mA) | | | | |
| maximum value | 12 | 14 | 15 | 15 |
| minimum value | 2 | 2 | 2 | 2 |

As is seen from the results shown in Table 1, the residual metal piece was completely dissolved out and removed if the electrolysis was conducted for 40 minutes. The length and weight of the above residual metal pieces would more than likely be larger than those of metal pieces that would actually be left in root canals of teeth under normal clinical conditions. Accordingly, it will readily be understood that residual metal pieces can be removed from root canals of teeth by this electrolytic implement of the present invention within a much shorter time than according to the conventional methods.

What is claimed is:

1. An electrolytic implement for removing a metal piece in the root canal of a tooth, comprising a positive electrode formed of a metal needle, said needle, except for a tip portion thereof, coated with an electrically insulating material, said tip portion adapted to come into contact with said metal piece; and a negative electrode formed by a metal tube coated, except for a tip portion thereof, with electrically insulating material; said metal needle fitting within the metal tube and being freely slidable therein.

2. An electrolytic implement as set forth in claim 1, wherein the metal needle has a pipe-like shape.

3. An electrolytic implement as set forth in claim 1, wherein both the metal needle and the metal tube are formed of a platinum-rhodium alloy.

4. An electrolytic implement as set forth in claim 3, wherein the platinum-rhodium alloy comprises 60 to 90% by weight of platinum and 10 to 40% by weight of rhodium.

5. An electrolytic implement as set forth in claim 1, wherein the electrically insulating material covering the outer faces of the metal needle and the metal tube is polyvinyl chloride.

6. An electrolytic implement as set forth in claim 1, wherein an absorbent piece is attached to the tip portion of the metal tube.

7. An electrolytic implement as set forth in claim 6, wherein the absorbent piece is formed of absorbent cotton.

8. A method of removing a metal piece left in the root canal of a tooth during dental surgery, comprising creating an electrolytic cell in said root canal by inserting a first electrode into and along said root canal until said electrode makes contact with said metal piece, supplying a physiologically acceptable electrolyte into said root canal into a space formed between and surrounding said first electrode, said metal piece and a second electrode spaced from the first electrode, and applying an electric potential to said electrodes such that the first electrode is the positive electrode to cause an electrolytic current to flow at a physiologically acceptable level until said metal piece is completely dissolved by electrolysis.

9. A method according to claim 8, wherein said electrolyte comprises a sodium chloride solution and said electrodes are formed of a platinum-rhodium alloy.

10. A method according to claim 8, wherein electrolysis is conducted under a voltage of from three to five volts and at an electrolysis current of from two to twenty mA.

* * * * *